United States Patent [19]

Kamachi et al.

[11] Patent Number: 4,935,508
[45] Date of Patent: Jun. 19, 1990

[54] PROCESS FOR CEPHEM PRODRUG ESTERS

[75] Inventors: Hajime Kamachi, Urayasu; Takaaki Okita, Tokyo; Satsuki Okuyama, Hachioji; Takayuki Naito, Kawasaki, all of Japan

[73] Assignee: Bristol-Myers Company, Wallingford, Conn.

[21] Appl. No.: 235,133

[22] Filed: Aug. 23, 1988

[51] Int. Cl.$^5$ ............................................. C07D 501/04
[52] U.S. Cl. ................................... 540/222; 540/221; 540/226
[58] Field of Search ................................ 540/222, 225

[56] References Cited

U.S. PATENT DOCUMENTS

| | | | |
|---|---|---|---|
| 4,196,205 | 4/1980 | Heymes et al. | 424/246 |
| 4,496,562 | 1/1985 | Takaya et al. | 514/207 |
| 4,559,334 | 12/1985 | Takaya et al. | 514/202 |
| 4,708,955 | 11/1987 | Iimura et al. | 514/202 |
| 4,714,760 | 12/1987 | Brundidge et al. | 540/222 |

FOREIGN PATENT DOCUMENTS 59-65095  4/1984  Japan .
2051066  1/1981  United Kingdom .

OTHER PUBLICATIONS

R. Bucourt, et al., Tetrahedron Letters, vol. 34, pp. 2233-2243 Amino-2-Thiazolyl-4-Acetyles.

*Primary Examiner*—Nicholas S. Rizzo
*Attorney, Agent, or Firm*—Robert E. Carnahan

[57] ABSTRACT

A process for the selective formation of oximino o-protected derivatives of lower alkyl 2-(2-aminothiazol-4-yl)-2-oximinoacetates, and their use in the acylation of 7-amino-cephalosporin compounds is disclosed.

9 Claims, No Drawings

PROCESS FOR CEPHEM PRODRUG ESTERS

FIELD OF THE INVENTION

This invention relates to the synthesis of cephem compounds having an additional hetero ring in the 7-position (Class 540, Subclass 225).

SUMMARY OF THE INVENTION

U.S. Pat. No. 4,708,955 (Iimura, et al. patented Nov. 24, 1987) is concerned with prodrug esters of the type illustrated in Formula I

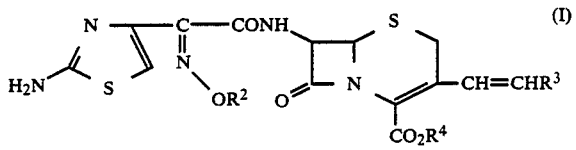

wherein $R^2$ is H, $R^3$ is methyl and $R^4$ is a physiologically hydrolyzable ester group. The invention described and claimed herein is concerned with an improved process for preparing the prodrug esters of Formula I wherein $R^2$ is H, $R^3$ is H or $CH_3$, and $R^4$ is a physiologically hydrolyzable ester group. The entire specification of U.S. Pat. No. 4,708,955 is incorporated herein by reference. Prodrug esters of Formula I, wherein $R^2$ and $R^3$ are H are disclosed in published Japanese Kokai Koho No. 59-89689 (July 15, 1984), and corresponding U.S. Pat. Nos. 4,559,334, and 4,409,214 patented Dec. 17, 1985 and Oct. 11, 1983, respectively.

BACKGROUND AND PRIOR ART

The method of U.S. Pat. No. 4,708,955 and of published Japanese Kokai Koho No. 59-116291 (U.S. Pat. No. 4,496,562) (July 15, 1984) and corresponding U.S. Pat. No. 4,496,562 patented Jan. 29, 1983 involve synthesis of the acid of Formula I wherein $R^2$, and $R^4$ are H, and then esterification thereof with the desired physiologically hydrolyzable ester group, $R^4$. This method is not suited for commercial scale development because chromatographic methods of purification are required and because the yield is low.

The present inventors have discovered that one reason for the low yield and purification difficulties in the foregoing esterification process is the formation of oximino O-substituted by-products, i.e. by-products wherein $R^2$ is an acyl substituent. Thus the esterification of an oximino O-protected intermediate was conceived of, and an examination of the prior art was made to ascertain whether suitable intermediates were available. The referenced patent itself, U.S. Pat. No. 4,708,955, provides N,O-diprotected intermediates of Formula IV

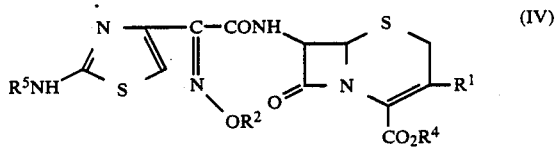

wherein $R^1$ is 1-propenyl, $R^2$ and $R^5$ are respectively O- and N-protecting groups such as the trityl group, and $R^4$ is a protective ester group such as diphenylmethyl. A further discovery of the present inventors is that removal of the $R^5$ trityl group is not a facile reaction, and is another reason for the poor overall yield in the synthesis of prodrug esters of Formula I via intermediates of Formula IV. Selective removal thereof in the presence of the desired $R^4$ physiologically hydrolyzable ester group was not therefore considered feasible in the present case, although analogous processes involving allegedly selective removal of $R^2$ and $R^5$ (Formula IV) protecting groups in the presence of an $R^4$ ester group have been reported. Such is shown in published Japanese Kokai Koho No. 56-8391 (Jan. 28, 1981) and corresponding published British specification GB 2,051,066 published Jan. 14, 1981 with respect to the compound of Formula IV wherein $R^1$ is methyl, $R^2$ and $R^5$ are trityl, and $R^4$ is pivaloyloxymethyl, and in published Japanese Kokai Koho No. 59-65095 (Apr. 13, 1984) wherein $R^1$ is $-SCH_3$ or $-SC_2H_5$, $R^2$ and $R^5$ are trityl, and $R^4$ is pivaloyloxymethyl, or 1-ethoxycarbonyloxyethyl.

Another method used to prepare prodrug esters of Formula I wherein $R^2$ and $R^3$ are H, and $R^4$ is a physiologically hydrolyzable ester group involves preparation of a 2-oximino-4-bromoacetoacetamido cephalosporin intermediate and conversion thereof to an aminothiazole by reaction with thiourea according to the following reaction scheme.

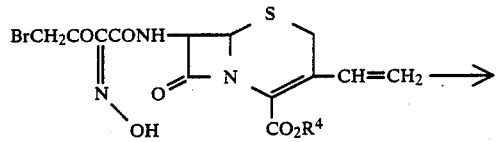

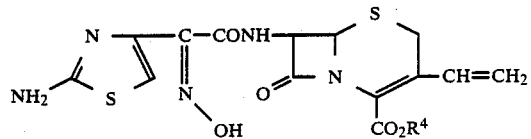

The foregoing scheme is described in published Japanese Kokai Koho No. 59-89689 (May 23, 1984) and corresponding U.S. Pat. No. 4,559,334 patented Dec. 17, 1985.

Stepwise hydrolytic deprotection of a cephalosporin ester of Formula IV wherein $R^1$ is the acetoxymethyl group, and $R^2$, $R^4$, and $R^5$ are protective groups to yield the O-protected acid (Formula IV wherein $R^4$ and $R^5$ are H, $R^2$ is trityl, and $R^1$ is acetoxymethyl) has been described in U.S. Pat. Nos. 4,196,205 (Apr. 1, 1980), refer to Column 45, lines 25-33. Prodrug esters were not the subject of this patent, however, and no attempt to esterify the foregoing acid was described.

Acylation of the 7-amino group of the 3-substituted ceph-3-em-4-carboxylate of Formula II by compounds of Formula III herein $R^2$ is methyl and AE is benzotriazol-1-yl is described in U.S. Pat. No. 4,714,760 (Brundige, et al. patented Dec. 22, 1987, column 9, line 4). The $R^2$ methyl group is not regarded in the art as a protecting group since it is neither a readily introduced nor a readily removed group.

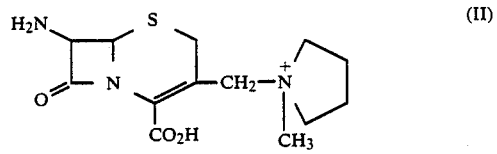

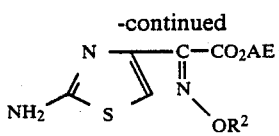

(III)

No example exists in the prior art of using an acylation active ester of Formula III wherein $R^2$ is a readily removable blocking group in cephalosporin antibiotic synthesis.

Bucourt, et al. have reported in Tetrahedron 34, 2233 (1978) that reaction of ethyl 2-(2-aminothiazol-4-yl)-2-hydroximinoacetate with one molecular proportion of trityl chloride in the presence of triethylamine yields selectively the N-trityl product. Two molecular proportions of trityl chloride yields the N,O-ditrityl product.

DETAILED DESCRIPTION OF THE INVENTION

The present invention provides a process for the synthesis of prodrug esters of Formula I wherein $R^2$ is hydrogen, $R^3$ is hydrogen or methyl, and $R^4$ is a physiologically hydrolyzable ester group which comprises esterification of an intermediate of Formula I, wherein $R^2$ is an O-protecting group of the type commonly used in the synthesis of cephalosporin compounds and thereafter removing said O-protecting group by conventional means. This is to be distinguished from prior art processes where the acid per se of Formula I wherein $R^2$ and $R^4$ are hydrogen is esterified, or wherein an N,O-diprotected intermediate of Formula IV is employed.

The physiologically hydrolyzable esters are those which are hydrolyzed following ingestion or injection to provide the carboxylate form of the antibiotic which is the most active form. They are preferably administered orally since hydrolysis occurs rapidly under the influence of the digestive enzymes. Parenteral administration is appropriate where hydrolysis of the ester will occur in the blood stream or other body tissue. Suitable esters are the pivaloyloxymethyl, 1-pivaloyloxyethyl, 3-phthalidyl, p-glycyloxybenzoyloxymethyl, and others illustrated in the examples appearing near the end of this specification.

An impediment to completing the present invention was the lack of description in the prior art of mono-O-blocked acylating agents of Formula III shown above in which $R^2$ is an O-protecting group of the type commonly used in the synthesis of cephalosporin compounds and AE is an acylation active ester group of the type commonly employed in organic synthesis to promote the acylation of amino compounds by carboxylic acyl groups. These intermediates of Formula III on reaction with intermediates of Formula VI yield intermediates of Formula I wherein $R^2$ is an O-protecting group, and $R^4$ is hydrogen.

The present inventors have found that selective protective etherification of the hydroximino group of ethyl 2-(2-aminothiazol-4-yl)-2-hydroxyimino acetate occurs when sodium hydride is employed as the base for the reaction of equal molar amounts of triphenylmethyl chloride and ethyl 2-(2-aminothiazol-4-yl)-2-hydroximinoacetate. This is contrary to the teaching of Bucourt, et al., cited above, according to which selective N-substitution occured on reaction of equal molar amounts of these reagents in the presence of triethylamine.

Other $R^2$ O-protecting groups in addition to the trityl group may be employed. Those which are commonly used in the synthesis of cephalosporin compounds are contemplated. Such groups are those which are introduced by readily available reagents and which are readily removed when desired by simple reaction under mild or ambient conditions, such as by hydrolysis or hydrogenolysis. Examples of suitable O-blocking groups are, in addition to trityl, (p-anisyl)-diphenylmethyl, methoxymethyl, 2-methoxyethoxymethyl, 1-methoxy-1-methylethyl, tertiary butyldimethylsilyl, etc.

The acid of Formula V and the lower alkyl and acylation active esters thereof wherein $R^2$ is an O-protecting group of the type commonly used in the synthesis of cephalosporin compounds are novel compounds and are considered part of the present invention.

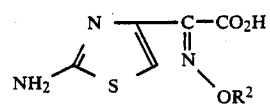

(V)

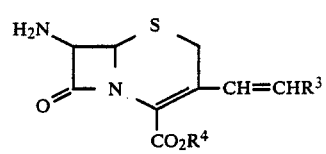

(VI)

The lower alkyl esters of the acid of Formula V have from 1 to 4 carbon atoms in the lower alkyl group. The acylation active esters are those esters containing a labile esterifying group which lend the qualities of an acylation agent for amino compounds to the resulting ester. Such esters are well-known in organic synthesis and include the esters of 1-hydroxybenzotriazole, ring substituted derivatives thereof, esters of 1-hydroxysuccinimide and derivates thereof, such as bicyclo[2.2.1-]hept-5-ene- 2,3-dicarboxylic acid 1-hydroxyimide, p-nitrophenyl, 2,4-dinitrophenyl, etc. The acylation active ester groups are referred to herein by the symbol AE.

The acylation of 7-amino-3-substituted ceph-3-em-4-carboxylic acids of Formula VI wherein $R^3$ is H or $CH_3$ with the active ester of Formula III is carried out in a known fashion to provide the mono-O-protected cephalosporin of Formula I in which $R^2$ is an O-protecting group of the type described above, $R^3$ is H or $CH_3$, and $R^4$ is H. It is preferred first to silylate the 7-amino group of the reactant of Formula VI by treatment with a conventional silylating agent such as trimethylsilyl chloride, trimethylsilyl bromide, bis-trimethylsilylacetamide, etc. To accomplish this, the reactant of Formula VI is dissolved in an appropriate aprotic solvent such as methylene chloride or tetrahydrofuran, treated with the silylating agent, and then the active ester of Formula III is added thereto. The silylation phase is carried out in the presence of triethylamine as acid scavenger. Silylation is carried out at a temperature of about 10° C. and the acylation step by means of the active ester at room temperature. The preferred solvent is tetrahydrofuran and the preferred silylation agent is trimethylsilyl chloride. These conditions afford a quantitative yield of the desired product having a purity of 96%.

The esterification may also be carried out in a conventional manner. For example, 1-acetoxyethyl bromide in the presence of potassium carbonate and dimethylformamide as reaction medium affords the desired 1-acetoxyethyl ester in 97% yield of material having a purity of 80%.

Deblocking by removal of the O-trityl group is carried out by hydrolysis preferably using 90% formic acid or 90% acetic acid. Trifluoroacetic acid may also be employed.

The present process offers the advantage over those of the prior art as represented by U.S. Pat. No. 4,708,955 of Iimura, et al. and of published Japanese Patent Kokai Koho No. 59-116291 (U.S. Pat. No. 4,496,562) of better yield and the elimination of chromatographic purification of either intermediates or end product. The following tabulation provides yield information for the preparation of various prodrug esters according to the present process as illustrated in the following examples in comparison to yields by the method of U.S. Pat. No. 4,708,955 applied to the preparation of the same compounds.

| TLC | thin layer chromatography |
|---|---|
| MIBK | methyl isobutyl ketone |
| MEK | methyl ethyl ketone |
| BSA | bis(trimethylsilyl)acetamide |

Procedure 1

Ethyl (Z)-2-(2-Aminothiazol-4-yl)-2-trityloxyiminoacetate

Sodium hydride (60% dispersion in mineral oil, 13.2 g, 0.33 mol) was added portionwise to a cold (0° C.) mixture of ethyl (Z)-(2-aminothiazol-4-yl)-2-hydroxyiminoacetate (64.5 g, 0.3 mol) in dry THF (1 L) with vigorous stirring and the mixture was stirred for 0.5 hr. at room temperature. To the mixture was added a solution of trityl chloride (92.0 g, 0.33 mol) in dry THF (0.2 L) with cooling and stirring. The mixture was stirred for 2 hr. at ambient temperature and evaporated under reduced pressure. Chloroform (1 L) was added to the residue and the mixture was washed with water. The

| Comparative Yields for Compounds of Formula I | | | | | | |
|---|---|---|---|---|---|---|
| Product | | | Process Yield | | | |
| | | | Herein from VI | | U.S. Pat. No. 4,708,955 from DPM ester of VI | |
| $R^2$ | $R^3$ | $R^4$ | ($R^3$ = Z—$CH_3$) | Proc. No. | ($R^3$ = Z—$CH_3$) | Ex. No. |
| H | $CH_3$ | —CHOCCH$_3$ with CH$_3$ and =O | 49% | 7,8,9 | 3% | 33,34,35 |
| H | $CH_3$ | —CH(CH$_3$)—OCO—cyclohexyl | 24% | 7,13,14 | 5% | 33,34,(1) |
| H | $CH_3$ | —CHOCOC$_2$H$_5$ with CH$_3$ and =O | 44% | 7,15,16 | 3% | 33,34,(2) |
| H | $CH_3$ | —CH$_2$— (dioxol-methyl, CH$_3$) | 51% | 7,17,18 | 5% | 33,34,(3) |

(1) The yield in the esterification step was 28%.
(2) The yield in the esterification step was 17%.
(3) The yield in the esterification step was 29%.

DESCRIPTION OF SPECIFIC EMBODIMENTS

Abbreviations Used

| THF | tetrahydrofuran |
|---|---|
| trityl | triphenylmethyl |
| HOBT | 1-hydroxybenzotriazole |
| DCC | dicyclohexylcarbodiimide |
| EtOAc | ethyl acetate |
| DMSO | dimethylsulfoxide |
| 1/34 | 7-amino-3-[(Z)-1-propenyl]-3-cephem-4-carboxylic acid |
| DMF | dimethylformamide |
| BuOAc | n-butyl acetate |
| HPLC | high performance liquid chromatography |
| TEA | triethylamine |
| TMSCl | trimethylsilyl chloride |
| MeOH | methanol | insoluble material was filtered and the organic layer of the filtrate was separated. The insoluble material was extracted again with a mixture of chloroform (300 ml) and methanol (50 ml) by sonication for 10 min. and subsequent filtration. The extract was combined with the separated organic layer and evaporated under reduced pressure. The residue was triturated with toluene (0.3 L) to crystallize the product as colorless prisms, which were collected by filtration, washed with a small toluene and dried in vacuo. Yield, 91.2 g (66%). The filtrate was evaporated and treated with toluene to give 19.2 g of the second crop.

Total yield, 110.4 g (80%). MP 181°–183° C.

IR $\nu_{max}$ (KBr)cm$^{-1}$ 3450, 1735, 1620. $^1$H NMR (60 MHz, CDCl$_3$) δ1.30 (3H, t, J=7 Hz, CH$_3$), 4.37 (2H, q, J=7 Hz, CH$_2$), 5.93 (2H, s, NH$_2$), 6.42 (1H, s, thiazole-H), 7.3 (15H, s, phenyl).

Anal Calcd for C$_{26}$H$_{23}$N$_3$O$_3$S 0.6 (CHCl$_3$): C 60.38, H 4.50, N 7.94, S 6.06.

Found: C: 60.68, H 4.38, N 7.95, S 6.10.

Procedure 2

(Z)-2-(2-Aminothiazol-4-yl)-2-trityloxyiminoacetic Acid

A mixture of the ester produced in Procedure 1 (107.4 g, 0.234 mol) and sodium hydroxide (28.1 g, 0.7 mol) in 50% aqueous dioxane (0.8 L) was heated under reflux for 1.5 hr. After cooling, the mixture was mixed with ethyl acetate (1 L), acidified to pH 4 with conc. hydrochloric acid (58 ml) and shaken. The organic layer was separated and washed with water (1 L). The aqueous layer was discarded and the organic layer was again washed with water (3 L). During the washing, the product crystallized out as colorless prisms, which were collected by filtration. The product was washed with water (0.2 L) and ethyl acetate (0.2 L) successively and dried in vacuo over phosphorous pentoxide.

Yield, 80.2 g (80%), MP 179°–182° C.

IR $\nu_{max}$(KBr) cm$^{-1}$ 3450, 1710, 1610, 1535. $^1$H NMR (60 MHz, DMSO-d$_6$) δ6.80 (1H, s, thiazole-H), 8.30 (15H, s, phenyl-H).

Anal Calcd for C$_{24}$H$_{19}$N$_3$O$_3$S.3/4 H$_2$O: C: 65.07, H 4.66, N 9.49, S 7.24.

Found: C 64.99, H 4.60, N 9.22, S 7.06.

Procedure 3

Benzotriazol-1-yl (Z)-((Z)-2-Aminothiazol-4-yl)-2-trityloxyiminoacetate

To a stirred solution of Z-(2-aminothiazol-4-yl)-2-trityloxyiminoacetic acid produced by Procedure 2 (143.6 g, 0.33 mol) and 1-hydroxybenzotriazole (HOBT) monohydrate (55.5 g, 0.36 mol) in tetrahydrofuran (3.2 L) was added dicyclohexylcarbodiimide (DCC) (74.8 g, 0.36 mol). The mixture was stirred at room temperature for 1 hr. and filtered. The filtrate was concentrated to a volume of ca. 500 ml and isopropyl ether (600 ml) was added to the concentrate to precipitate the product as a crystalline solid, which was collected by filtration, washed with isopropyl ether, and dried to give 184.1 g (100%) of the title compound. MP 186°–190° C. IR $\nu_{max}$(KBr) cm$^{-1}$ 1815, 1620, 1540. $^1$H NMR (60 MHz, DMSO-d$_6$) δ7.0–8.5 (aromatic, 19H).

Procedure 4

Ethyl (Z)-2-(2-Aminothiazol-4-yl)-2-(p-diphenylmethoxyiminoacetate

To a cooled suspension of ethyl (Z)-2-(2-aminothiazol-4-yl)-2-hydroxyiminoacetate (2.15 g, 10 mmol) in dry THF (33 ml) was added NaH (60%, 450 mg, 11.3 mmol) and the mixture was stirred for 40 min. at ambient temperature. The mixture was cooled in ice bath and to the suspension was added a solution of (p-anisyl)-diphenylmethyl chloride (3.40 g, 11.0 mmol) in THF (7 ml). The mixture was stirred for 1 hr. at room temperature and evaporated. To the residue was added water (10 ml) and the mixture was extracted with EtOAc (20 ml). The extract was evaporated under reduced pressure and the residue was dissolved in toluene. The insolubles were filtered off and the filtrate was evaporated under reduced pressure. Crystallization of the residue from ether-n-hexane-EtOAc gave 3.44 g (71%) of the product. MP 188°–191° C.

IR $\nu_{max}$(KBr) cm$^{-1}$ 3440, 3100, 1740, 1620. $^1$H NMR (CDCl$_3$) δ 1.25 (3H, t, J=8 Hz, CH$_3$), 3.75 (3H, s, OCH$_3$), 4.35 (2H, q, J=8 Hz, CH$_2$), 5.93 (2H, s, NH$_2$), 6.42 (1H, s, thiazole-H), 6.75 (2H, d, J=10 Hz, phenyl), 7.20 (2H, d, J=10 Hz, phenyl), 7.25 (10H, s, phenyl).

Anal Calcd for C$_{27}$H$_{25}$N$_3$O$_4$S: C 66.51, H 5.17, N 8.62, S 6.58.

Found: C 66.84, H 5.33, N 8.48, S 6.51.

Procedure 5

(Z)-2-(2-Aminothiazol-4-yl)-2-(p-anisyl)diphenylmethoxyiminoacetic Acid

A mixture of the ester produced in Procedure 4 (3.20 g, 6.56 mmol) and NaOH (788 mg, 19.7 mmol) in dioxane-water (1:1, 23 ml) was heated under reflux for 40 min. After cooling, EtOAc (30 ml) was added and the mixture was acidified to pH 4 with dil. HCl. The mixture was washed with water (30 ml ×3). During the course of washing, the desired product precipitated in the organic layer. The product was collected by filtration and dried.

Yield 1.80 g (60%)

MP 164° C. (grad. dec.).

IR $\nu_{max}$(KBR) cm$^{-1}$ 3400, 3280, 1670, 1610, 1510. $^1$H NMR (DMSO-d$_6$) δ3.70 (3H, s, OCH$_3$), 6.65 (1H, s, thiazole-H), 6.83 (2H, d, J=9 Hz, phenyl), 7.05–7.30 (12H, phenyl).

Procedure 6

Benzotriazol-1-yl (Z)-2-(2-Aminothiazol-4-yl)-2-(p-anisyl) diphenylmethoxyiminoacetate To a mixture of the acid produced in Procedure 5 (1.67 g, 3.63 mmol) and HOBT monohydrate (612 mg, 4.00 mmol) in THF (37 ml) was added DCC (824 mg, 4.00 mmol) and the mixture was stirred for 1 hr. at room temperature and filtered. The filtrate was concentrated and the residue was triturated with isopropyl ether to give 1.50 g (71%) of the desired product as an amorphous powder.

MP 167°–169° C.

IR $\nu_{max}$(KBr) cm$^{-1}$ 3460, 3070, 1820, 1620, 1540. $^1$H NMR (CDCl$_3$+DMSO-d$_6$) δ3.80 (3H, s, OMe), 6.80 (1H, s, thiazole-H), 6.82 (2H, d, J=10 Hz, phenyl), 7.03 (2H, s, NH$_2$), 7.2–7.5 (16H, phenyl).

Procedure 7

7-[(Z)-2-(2-Aminothiazol-4-yl)-2-trityloxyiminoacetamido]-3-[(Z)-1-propenyl]-3-cephem-4-carboxylic Acid Triethylamine (44.6 g, 441 mmol) was added to a suspension of 7-amino-3-[(Z)-1-propenyl]-3-cephem-4-carboxylic acid (1/34) (48.1 g, 200 mmol) in dry THF (960 ml). Trimethylsilyl chloride (54.6 g, 503 mmol) was added dropwise to the cold mixture (10° C.) during a period of 5 minutes. The mixture was stirred for 30 min. at room temperature and cooled again to ca. 10° C. To the mixture was added a solution of benzotriazol-1-yl 2-[(Z)-2-aminothiazol-4-yl]-2-trityloxyiminoacetate (Procedure 3) (109.5 g, 200 mmol) in DMF (400 ml) during 2 min. The mixture was stirred overnight at room temperature and concentrated under reduced pressure to remove most of the THF. The concentrate was poured into ice-water (5 L) with vigorous stirring to separate the desired product, which was collected by filtration, washed with 2 L of water, and dried in vacuo, yield 131 g (100%, purity 96%).

IR $\nu_{max}$ (KBr) cm$^{-1}$ 1782, 1684, 1617. UV $\lambda_{max}$ (EtOH) nm ($\epsilon$) 290 (14700). $^1$H NMR (80 MHz, DMSO-d$_6$) $\delta$1.75 (3H, dd, J=1, 7 Hz, CH—CH$_3$), 3.55 (2H, ABq, 2-H), 5.13 (1H, d, J=5 Hz, 6-H), 5.72 ($^1$H, dd, J=5, 9 Hz, 7-H), 6.60 (1H, s, thiazole-H), 7.0–7.5 (15H, brs, Ph).

Procedure 8

1-Acetoxyethyl 7-[(Z)-2-(2-Aminothiazol-4-yl)-2-trityloxyiminoacetamido]-3-[(Z)-1-propenyl]-3-cephem-4-carboxylate To a cooled solution of the product of Procedure 7 (34.4 g, 52.8 mmol) and well-milled K$_2$CO$_3$ (7.24 g, 52.8 mmol) in dry DMF (344 ml) was added 1-acetoxyethyl bromide (17.64 g, 105.6 mmol) at 0° C. under argon and the mixture was stirred at about 5° C. for 65 min. The reaction mixture was poured into ice-water (1720 ml) with stirring adjusted to pH 7 with aq. NaHCO$_3$ solution, and stirred for 30 min. The resulting precipitate was collected, washed with water (100 ml) and dried to give 37.61 g of the desired product (97%, purity 80%) as an amorphous powder.

IR $\nu_{max}$ (KBr) cm$^{-1}$ 1780, 1760, 1680. UV $\lambda_{max}$ (EtOH) nm ($\epsilon$) 289 (13600). $^1$H NMR (80 MHz, CDCl$_3$) 6 1.52 (3H, d, J=6 Hz, CH—CH$_3$), 1.63 (3H, d, J=7 Hz, =CH—CH$_3$), 2.05 (3H, s, COCH$_3$), 3.28 (2H, ABq, 2-H), 5.05 ($^1$H, d, J=5 Hz, 6-H), 6.61 ($^1$H, s, thiazole), 7.0–7.5 (15H, brs, aromatic). Five grams of the amorphous product was chromatographed on a column of silica gel (Kiesel gel 60, 100 g). The column was eluted with CH$_2$Cl$_2$ and then CH$_2$Cl$_2$ containing 1% MeOH. The fractions containing the product were evaporated to give 2.23 g of product, again as an amorphous powder, which was crystallized from benzene-cyclohexane to give 1.60 g (32%) of crystalline product.

MP 136°–138° C.

Anal Calcd for C$_{38}$H$_{35}$N$_5$O$_7$S$_2$.1/2H$_2$O: C61.11, H 4.86, N 9.38, S 8.59.

Found: C 60.96, H 4.73, N 9.37, S 8.46.

Procedure 9

1-Acetoxyethyl 7-[(Z)-2-(2-Aminothiazol-4-yl)-2-hydroxyiminoacetamido]-3-[(Z)-1-propenyl]-3-cephem-4-carboxylate The amorphous product of Procedure 8 (1.0 g) was stirred in 90% formic acid (3 ml) for 50 min. at 25° C. The reaction mixture was filtered, the filtrate was poured into ice-water (40 ml) and the mixture was adjusted to pH 4 with 50% aq. NaOH. EtOAc (40 ml) was added without mixing to provide a two-phase system, and the aqueous layer was adjusted to pH 6 with aq. NaHCO$_3$ with vigorous stirring. The organic layer was separated, washed with water and dried over MgSO$_4$. Charcoal (100 mg) was added, the mixture was filtered, and the filtrate was evaporated under reduced pressure. The residue (Z/E=8/1) was dissolved in MeOH-CHCl$_3$(1=4, 12 ml). The solution was diluted with BuOAc (3 ml), concentrated to 4 ml and seeded. From the solution, 344 mg (51% yield) of the title compound (Z-propenyl/E-propenyl =16/1) was obtained. MP 146° C. (dec.).

IR $\nu_{max}$ (KBr) cm$^{-1}$ 1780, 1760, 1630. UV $\lambda_{max}$ (EtOH) nm ($\epsilon$) 222 (18900), 286 (12100).

Anal Calcd for C$_{19}$H$_{21}$N$_5$O$_7$S$_2$.1/2(BuOAc): C 47.73, H 4.92, N 12.65, S 11.58.

Found: C 47.73, H 4.82, N 12.81, S 11.66.

HPLC and $^1$H NMR (400 MHz) of crystalline title compound showed that it is a 1:1 mixture of R and S diastereo-isomers in regard to the 1-acetoxyethyl ester group. $^1$H NMR (400 MHz, DMSO-d$_6$) 67 1.43 (1.5 H, d, J=5.5 Hz CHMe), 1.44 (1.5H, d, J=5.5 Hz, CHMe), 1.59 (1.5H, dd, J=1.8, 7.0 Hz, CH=CHMe), 1.60 (1.5H, dd, J=1.8, 7.3 Hz, CH=CHMe), 2.05 (1.5H, s, OAc), 2.07 (1.5H, s, OAc), 3.52 (0.5H, d, J=18 Hz, 2-H), 3.54 (0.5 H, d, J=18 Hz, 2-H), 3.59 (0.5H, d, J=18 Hz, 2-H), 3.61 (0.5 H, d, J=18 Hz, 2-H), 5.22 (0.5H, d, J=4.8 Hz, 6-H), 5.24 (0.5H, d, J=4.8 Hz, 6-H), 5.62–5.74 (1H, m, CH=CHMe), 5.80 (0.5H, dd, J=4.8, 8.0 Hz, 7-H), 5.83 (0.5H, dd, J=4.8, 8.0 Hz, 7-H), 6.07 (0.5H, dd, J=10.8, 1.8 Hz, CH=CHMe), 6.09 (0.5H, dd, J=10.8, 1.8 Hz, CH=CHMe), 6.65 (0.5H, s, thiazole-H), 6.66 (0.5H, s,thiazole-H), 6.83 (0.5H, q, J=5.5 Hz, CHMe), 6.93 (0.5H, q, J=5.5 Hz, CHMe), 7.11 (2H, s, NH$_2$), 9.45 (0.5H, d, J=8 Hz, 7-CONH), 9.47 (0.5H, d, J=9 Hz, 7-CONH), 11.291 (0.5H, s, NOH), 11.293 (0.5H, s, NOH).

Procedure 10

7-[(Z)-2-(2-Aminothiazol-4-yl)-2-(p-anisyl)diphenylmethoxyiminoacetamido]-3-[(Z)-1-propenyl]-3-cephem-4-carboxylic Acid To a cooled mixture of 1/34 (481 mg, 2.0 mmol) and TEA (446 mg, 4.4 mmol) in THF (12 ml) was added TMSCl (556 mg, 5.1 mmol) under argon atmosphere and the mixture was stirred for 30 min. at room temperature. The mixture was cooled in ice-water bath and a solution of the active HOBT ester produced in Procedure 6 (1.15 g, 2.0 mmol) in DMF (4 ml) was added. The mixture was stirred overnight at room temperature and concentrated under reduced pressure. The residue was poured into ice-water and the precipitate was collected by filtration to give 1.30 g (65%) of the product as an amorphous powder. Estimated purity 89% (by HPLC).

MP 155° C. (grad. dec.).

IR $\nu_{max}$ (KBr) cm$^{-1}$ 1780, 1680, 1630, 1580. UV $\lambda_{max}$ (EtOH) nm ($\epsilon$, $_1$ cm, $^1$%) 284 (15,000). $^1$H NMR (CDCl$_3$) $\delta$1.70 (3H, dd, J=6, 1 Hz, CH$_3$), 3.35 (2H, brs.,2-H), 3.75 (3H, s, OCH$_3$), 5.10 (1H, d, J=5 Hz, 6-H), 5.5–6.0 (2H, m, 7-H, 3-CH=CH-), 6.25 ($^1$H, dd, J=12, Hz, 3-CH=), 6.68 ($^1$H, s, thiazole-H), 6.30 (2H, d, J=9 Hz, phenyl), 7.2–7.4 (12H, s, phenyl), 7.95 (1H, d, J=10 Hz, NH).

Procedure 11

1-Acetoxyethyl 7-(Z)-2-(2-Aminothiazol-4-yl)-2-(p-anisyl) diphenylmethoxyiminoacetamido]-3-[(Z)-1-propenyl]-3-cephem-4-carboxylate To a cooled (5° C.) mixture of the product of Procedure 10 (1.28 g, 1.9 mmol) in dry DMF (11 ml) was added K$_2$CO$_3$ (259 mg, 1.9 mmol) under argon atmosphere and 1-acetoxyethyl bromide (684 mg, 4.1 mmol) was added. The mixture was stirred for 60 min. at 5° C. and poured into ice-water (80 ml) and the pH was adjusted at pH 7 by addition of aq. NaHCO$_3$. The product was collected by filtration and chromatographed on a column of silica gel (25 g). The column was eluted with n-hexane-EtOAc and the fraction containing the desired product was evaporated under reduced pressure to give 895 mg (62 %) of the desired product. MP 127°–132° C.

IR $\nu_{max}$ (KBr) cm$^{-1}$ 1790, 1770, 1540, 1510. UV $\lambda_{max}$ (EtOH) nm ($\epsilon$) 286 (15,000). $^1$H NMR (CDCl3) δ 1.53 (1.5H, d, J=5.5 Hz, CHCH3), 1.55 (1.5H, d J=5.5 Hz, CHCH3), 1.65 (1.5H, dd, J=1.8, 4.8 Hz, =CHCH3), 1.67 (1.5H, dd, J=1.8, 4.4 Hz, =CHCH3), 2.09 (1.5H, s, OAc), 2.10 (1.5H, s, OAc), 3.22 (0.5H, d, J=18.0 Hz, 2-H), 3.25 (0.5H, d, J=18.0 Hz, 2-H), 3.31 (0.5H, d, J=18.7 Hz, 2-H), 3.40 (0.5H, d, J=18.7 Hz, 2-H), 3.77 (1.5H, s, OMe), 3.78 (1.5H, s, OMe), 5.07 (0.5H, 7d, J=5.1 Hz, 6-H), 5.09 (0.5H, d, J=5.1 Hz, 6-H), 5.70–5.79 (1H, m, CH=CHMe), 5.89 (0.5H, dd, J=5.1, 8.4 Hz, 7-H), 5.93 (0.5H, dd, J=5.1, 8.4 Hz, 7-H), 6.17 (0.5H, dd, J=12, 1.5 Hz, 3-CH=), 6.18 (0.5H, dd, J=12, 1.5 Hz, 3-CH=), 6.47 (0.5H, d, J=8.4 Hz, CONH), 6.53 (0.5H, d, J=8.4 Hz, CONH), 6.66 (0.5H, s, thiazole-H), 6.67 (0.5H, s, thiazole-H), 6.83 (2H, d, J=9.6 Hz, phenyl), 6.97 (0.5H, q, J=5.5 Hz, CHCH3), 7.04 (0.5H, q, J=5.5 Hz, CHCH3), 7.21 (2H, dd, J=1.8, 9.6 Hz, phenyl), 7.31 (5H, s, phenyl), 7.32 (5H, s, phenyl).

Anal Calcd for $C_{39}H_{37}N_5O_8S_2 \cdot 1/5C_6H_{14}$: C 61.50, H 5.11, N 8.92, S 8.17.

Found: C 61.99, H 5.04, N 8.70, S 7.71

Procedure 12

1-Acetoxyethyl 7-[(Z)-2-(2-Aminothiazol-4-yl)-2-hydroxyiminoacetamido]-3-[(Z)-1-propenyl]-3-cephem-4-carboxylate A mixture of the product of Procedure 11 (300 mg) and 90% acetic acid (6 ml) was stirred for 1 hr. at 25° C. The mixture was cooled in ice-bath and adjusted to pH 4 with 50% aq. NaHCO3 with stirring. The organic layer was separated, washed with water and dried. After evaporation, the residue was dissolved in MeOH-CHCl3(1:4, 1.2 ml). BuOAc (1.1 ml) was added and the solution was concentrated to about 1.2 ml. The concentrate was seeded and allowed to stand in a refrigerator to give 82 mg (42%) of the crystalline product (Z/E=15/1).

Procedure 13

1-Cyclohexyloxycarbonyloxyethyl 7-[(Z)-2-(2-Aminothiazol-4-yl)-2-trityloxyiminoacetamido]-3-[(Z)-1-propenyl]-3-cephem-4-carboxylate To a mixture of the product of Procedure 7 (35 g, 53.7 mmol) 18-crown-6 (4.0 g, 15 mmol) and well ground K2CO3 (9.45 g, 6.84 mmol) in dry DMF (330 ml) was added dropwise the cyclohexyl 1-iodoethyl carbonate (41 g, 138 mmol) at 0° C. under argon and the mixture was stirred for 1 hr. at 2°–4° C. The mixture was diluted with ethyl acetate (1.5 L) and washed well with water. The organic layer was separated, dried and evaporated under reduced pressure. The residue was chromatographed on a column of silica gel (400 g) and the column was eluted with n-hexane-dichloromethane (2:1 to 0:1). The fractions containing the desired product were combined and evaporated under reduced pressure to afford 27.3 g (62%) of the product as an amorphous powder.

IR $\nu_{max}$ (nuj) cm$^{-1}$ 1785, 1750, 1670, 1620. $^1$H NMR (80 MHz, CDCl3) δ1.0–2.0 (16H, m, cyclohexyl, two methyls), 3.3 (2H, 2-H), 5.05 (1H, d, J=5 Hz, 6-H), 5.5–6.0 (4H, m, vinyl-H, 7-H, NH2), 6.15 (1H, d, J=12 Hz, vinyl-H), 6.62 (1H, s, thiazole-H), 7.5 (15H, m, phenyl).

Procedure 14

1-Cyclohexyloxycarbonyloxyethyl 7-[(Z)-2-(2-Aminothiazol-4-yl)-2-hydroxyiminoacetamido]-3-[(Z)-1-propenyl]-3-cephem-4-carboxylate A mixture of the product of Procedure 13 (62.7 g, 0.076 mol) and 90% aqueous formic acid (110 ml) was stirred at room temperature for 1 hr. The reaction mixture was diluted with EtOAc (600 ml) and ice-water (300 ml) and the lower layer was adjusted to pH 3.3 with 30% aq. NaOH under vigorous stirring. The upper layer was diluted to 2 L, separated, washed with water (500 ml×3) and brine, dried over MgSO4 and concentrated under diminished pressure. The residue was dissolved in toluene (300 ml) which was carefully transferred to the top surface of a silica gel column (Wakogel C-200, 800 g). The column was eluted with CH2Cl2, 0.5%, 1.0%, 1.5%, 2.0% and 3.0% MeOH in CH2Cl2, successively. The fractions which exhibited approximately Rf: 0.12 on TLC (SiO2, 5% MeOH-CH were combined and concentrated in vacuo to give 30.0 g (68%) of the desired product as an amorphous powder. The starting material was recovered (8.4 g, 14%) from the fractions which showed Rf 0.55 on TLC.

The amorphous powder (35 g) was dissolved in methyl isobutyl ketone (280 ml) and the solution was allowed to stand overnight in a refrigerator. The colorless crystals were filtered off, washed with a small portion of MIBK at 5° C. (in a cold room) and dried to give 19.0 g (56%) of the crystalline product.

MP 120°–123° C. Z/E ratio (HPLC), 15/1.

IR $\nu_{max}$ (KBr) cm$^{-1}$ 2940, 1760, 1680, 1615. UV $\lambda_{max}$ (EtOH) nm ($\epsilon$) 287 (12,000). $^1$H NMR (400 MHz, DMSO-d6) δ1.2–1.8 (10H, m, cyclohexane), 1.46 (3H, d, J=5 Hz, CH-CH3), 1.60 (3H, dd, J=2, 8 Hz, =CH-CH3), 2.06 (3H, s, COCH3), 3.53 (1H, brs, 2-H), 4.55 ($^1$H, m, cyclohexane), 5.20 (1H, d, J=4 Hz, 6-H), 5.70 (1H, dd, J=4, 7 Hz, 7-H), 6.08 (1H, d, J=11 Hz, 3-CH=), 6.65 (1H, s, thiazole).

Procedure 15

1-Ethoxycarbonyloxyethyl 7-[(Z)-2-(2-Aminothiazol-4-yl)-2-trityloxyiminoacetamido]-3-[(Z)-1-propenyl]-3-cephem-4carboxylate To a cooled mixture of the product of Procedure 7 (2.06 g, 3.16 mmol), K2CO3 (644 mg, 4.7 mmol) and 18-crown-6 (248 mg, 0.94 mmol) in DMF (20 ml) was added 1-ethyoxycarbonyloxyethyl iodide (3.06 g, 12.6 mmol) at 5° C. and the mixture was stirred for 30 min. at the same temperature under argon atmosphere. The reaction mixture was poured into ice-water and extracted with EtOAc. The extracts were chromatographed on a column of silica gel and the column was eluted with CH2Cl2 containing 1%.MeOH. The fractions containing the desired product were evaporated to give 1.57 g (65%) of the product.

IR $\nu_{max}$ (KBr) cm$^{-1}$ 1760, 1685. UV $\lambda_{max}$ (EtOH) nm ($\epsilon$) 290 (11,200).

Procedure 16

1-Ethoxycarbonyloxyethyl 7-[(Z)-2-(2-Aminothiazol-4-yl)-2-hydroxyiminoacetamido]-3-[(Z)-1-propenyl]-3-cephem-4-carboxylate A mixture of the product of Procedure 15 (1.55 g, 2.02 mmol) and 90% formic acid (3 ml) was stirred for 1 hr at room temperature and diluted with EtOAc-ice-water. The mixture was adjusted to pH 3.5 with 30% NaOH below 10° C. The organic layer was separated, washed with water, dried and concentrated under reduced pressure. The residue was chromatographed on a column of silica gel. The column was eluted with n-hexane-EtOAc and the fraction containing the desired product was evaporated to give 712 mg (67%) of the desired product.

IR $\nu_{max}$ (KBr) cm$^{-1}$ 3325, 1760, 1685. UV $\lambda_{max}$ (EtOH) nm ($\epsilon$) 286 (12,700). $^1$H NMR (DMSO-d$_6$) 67 1.23 (3H, t, J=8 Hz, CH$_2$CH$_3$), 1.44 (3H, d, J=6 Hz, CHCH$_3$), 1.59 (3H, dd, J=1, 7 Hz, CH=CH-CH$_3$), 3.55 (2H, brs, 2-H), 4.15 (2H, q, J=8 Hz, CH$_2$CH$_3$), 5.17 (0.5H, d, J=5 Hz, 6-H), 5.24 (0.5 H, d, J=5 Hz, 6-H), 5.4–5.8 (1H, m, 3-CH=CH), 6.08 (1H, d, J=11 Hz, 3-CH=CH), 6.62 (1H, s, thiazole), 6.71 (1H, m, CHCH$_3$), 7.01 (2H, brs, NH$_2$), 9.40 (1H, d, J=8 Hz, CONH), 11.20 (1H, brs, OH).

Procedure 17

(5-Methyl-2-oxo-1,3-dioxolen-4-yl)methyl 7-[(Z)-2-(2-Aminothiazol-4-yl)-2-trityloxyiminoacetamido]-3-[(Z)-1-propenyl]-3-cephem-4-carboxylate To a cooled mixture of the product of Procedure 7 (2.06 g, 3.16 mmol), K$_2$CO$_3$ (640 mg, 9.4 mmol) and 18-crown-6 (248 mg, 0.94 mmol), in DMF (20 ml) was added (5-methyl-2-oxo-1, 3-dioxolen-4-yl)methyl bromide (1.8 g, 9.4 mmol) at 5° C. and the mixture was stirred for 30 min. at the same temperature under argon atomosphere. The reaction mixture was poured into ice-water and extracted with EtOAc. The extracts were chromatographed on a column of silica gel and the column was eluted with CHCl$_3$ containing 1% MeOH. The fractions containing the desired product were evaporated to give 2.11 g (87%) of the product.

IR $\nu_{max}$ (KBr) cm$^{-1}$ 2360, 2340, 1820, 1785, 1680.

UV $\lambda_{max}$ (EtOH) nm ($\epsilon$) 294 (13,100). $^1$H NMR (DMSO-d$_6$) $\delta$1.56 (3H, dd, J=2, 8 Hz, CH$_3$), 2.15 (3H, s, CH$_3$), 3.52 (2H, brs, 2-H), 5.06 (2H, ABq, COCH$_2$), 5.20 (1H, d, J=5 Hz, 6-H), 5.50 (1H, m, 3-CH=CH), 5.73 (1H, dd, J=5, 8 Hz, 7-H), 6.01 (1H, d, J=11 Hz, 3-CH=CH), 6.65 (1H, s, thiazole), 7.3 (15H, s, trityl).

Procedure 18

(5-Methyl-2-oxo-1,3-dioxolen-4-yl)methyl 7-[(Z)-2-(2-Aminothiazol-4-yl)-2-hydroxyiminoacetamido]-3-[(Z)-1-propenyl]-23-cephem-4-carboxylate A mixture of the product of Procedure 17 (2.0 g, 2.61 mmol) and 90% formic acid (4 ml) was stirred for 1 hr. at room temperature and diluted with EtOAc-ice-water. The mixture was adjusted to pH 3.5 with 30% NaOH with cooling below 10° C. The organic layer was separated, washed with water, dried and concentrated under reduced pressure. The residue was chromatographed on a column of silica gel. The column was eluted with CHCl$_3$ containing 1-3% MeOH and the fraction containing the desired product was evaporated and the residue was crystallized from MEK to give 807 mg (59%) of the product.

MP 121°–123° C.

IR $\nu_{max}$ (KBr) cm$^{-1}$ 2360, 2340, 1820, 1770. UV $\lambda_{max}$ (EtOH) nm ($\epsilon$) 286 (16,300). $^1$H NMR (DMSO-d$_6$) $\delta$1.55 (3H, dd, J=2, 8 Hz, CH$_3$), 2.15 (3H, s, =C-CH$_3$), 3.55 (2H, brs, 2-H), 5.08 (2H, ABq, COOCH$_2$), 5.20 (1H, d, J=5 Hz, 6-H), 5.50 (1H, m, 3-CH=CH), 5.76 (1H, dd, J=5, 8 Hz, 7-H), 6.07 (1H, d, J=11 Hz, 3-CH=CH), 6.62 (1H, s, thiazole), 7.05 (2H, brs, NH$_2$), 9.38 (1H, d, J=8Hz, CONH).

Procedure 19

7-[(Z)-2-(2-Aminothiazol-4-yl)-2-trityloxyiminoacetamido]-3-vinyl-3-cephem-4-carboxylic Acid A mixture of 7-amino-3-vinyl-3-cephem-4-carboxylic acid (3.2 g, 14.2 mmol) and BSA (11.5 ml, 56 mmol) in dry CH$_2$Cl$_2$ (75 ml) was stirred for 10 min. The active ester produced by Procedure 3 (8.78 g, 15.6 mmol) was added to the suspension and the mixture was stirred overnight at room temperature to be a brown solution. The mixture was concentrated and the concentrate was diluted with EtOAc-THF (1:1). The mixture was washed with aq. saturated NaCl, dried and concentrated. The residue was chromatographed on a silica gel column (Wakogel C-200, 110 g). The column was eluted with CH$_2$Cl$_2$ containing 5% of MeOH and the fractions containing the desired product were concentrated to give 6.3 g (70%) of the product.

IR $\nu_{max}$ (KBr) cm$^{-1}$ 3400, 1770, 1730. UV $\lambda_{max}$ (EtOH) nm ($\epsilon$) 290 (12,400). $^1$H NMR (DMSO-d$_6$) $\delta$3.55 (2H, ABq, 2-H), 5.13 (1H, d, J=5 Hz, 6-H), 5.1–5.8 (3H, m, CH=CH$_2$), 5.72 (1H, dd, J=5, 8 Hz, 7-H), 6.6 (1H, s, thiazole), 7.3 (15H, s, phenyl), 9.77 (1H, d, J=8 Hz, CONH).

Procedure 20

1-Ethoxycarbonyloxyethyl 7-[(Z)-2-(2-Aminothiazol-4-yl)-2-trityloxyiminoacetamido]-3-vinyl-3-cephem-4-carboxylate To a cooled mixture of the acid produced in Procedure 19 (2.0 g, 3.16 mmol), 18-crown-6 (248 mg, 0.94 mmol) and K$_2$CO$_3$ (644 mg, 4.7 mmol) was added 1-ethoxycarbonyloxyethyl iodide (5.0 g) under nitrogen atmosphere at 5° C. The mixture was stirred for 1 hr. at the same temperature and diluted with EtOAc-ice water. The organic layer was washed with water, dried and concentrated and the residue was chromatographed on a silica gel column (Silica gel 60, 50 g). The column was eluted with CH$_2$Cl$_2$ containing 1% MeOH and the fraction containing the desired product was concentrated to give 1.24 g (53%) of the product.

IR $\nu_{max}$ (KBr) cm$^{-1}$ 1780, 1760, 1680. $^1$H NMR (DMSO-d$_6$) $\delta$ 1.24 (3H, t, J=8 Hz, CH$_2$CH$_3$), 1.45 (3H, d, J=6 Hz, CHCH3), 3.62 (2H, ABq, 2-H), 4.15 (2H, q, J=8 Hz, CH$_2$CH$_3$), 5.18 (1H, d, J=5 Hz, 6-H), 5.1–5.8 (3H, m, CH=CH$_2$), 5.8 (1H, dd, J=5, 8 Hz, 7-H), 6.6 (1H, s, thiazole), 6.73 (1H, m, CH-CH$_3$), 7.3 (15H, s, phenyl), 9.40 (1H, d, J=8 Hz, CONH).

Procedure 21

1-Ethoxycarbonylethyl 7-[(Z)-2-(2-Aminothiazol-4-yl)-2-hydroxyiminoacetamido]-3-vinyl-3-cephem-4-carboxylate A mixture of the above cephem ester of Procedure 20 (1.21 g, 1.60 mmol) and 90% formic acid (2.4 ml) was stirred for 1 hr. at room temperature and diluted with EtOAc-ice water. The organic layer was separated, washed with water, dried and concentrated under reduced pressure. The residue was chromatographed on a column of silica gel and the column was eluted with chloroform containing 3% MeOH. The fraction containing the desired product was concentrated. The residue was crystallized from EtOAc to give 610 mg (74%) of the product.

MP 133°–135° C.

IR $\nu_{max}$(KBr) cm$^{-1}$ 3300, 1790, 1760, 1670. UV $\lambda_{max}$ (EtOH) nm ($\epsilon$) 224, (12,700), 292 (18,100). $^1$H NMR (DMSO-d$_6$) $\delta$1.24 (3H, t, J=8 Hz, CH$_2$CH$_3$), 1.46 (3H, d, J=6 Hz, CHCH$_3$, 3.73 (2H, ABq, 2-H), 4.15 (2H, q, J=8 Hz, CH$_2$CH$_3$), 5.15 (0.5H, d, J=5 Hz, 6-H), 5.22 (0.5H, d, J=5 Hz, 6-H). 5.1–5.8 (3H, m, CH=CH$_2$), 5.76 (0.5H, dd, J=5, 8 Hz, 7-H), 5.83 (0.5H, dd, J=5, 8 Hz, 7-H), 6.6 (1H, s, thiazole), 6.79 (1H, m, CH-CH$_3$), 7.00 (2H, brs, NH$_2$), 9.40 (1H, d, J=8 Hz, CONH), 11.25 (1H, s, OH).

Anal. Calcd for C$_{19}$H$_{21}$N$_5$O$_8$S$_2$.1/4 H$_2$O: C 44.22, H 4.14, N 13.69, S 12.43.

Found: C 44.21, H 4.08, N 13.64, S 12.21.

Procedure 22

(5-Methyl-2-oxo-1,3-dioxolen-4-yl)methyl 7-[(Z)-2-(2-Aminothiazol-4-yl)-2-trityloxyiminoacetamido]-3-vinyl-3-cephem-4-carboxylate To a stirred mixture of the product of Procedure 19 (2.0 g, 3.16 mmol), K$_2$CO$_3$ (644 mg, 4.7 mmol) and 18-crown-6 (248 mg, 0.44 mmol) in DMF (20 ml) was added (5-methyl-2-oxol, 3-dioxolen-4-yl)methyl bromide (1.81 g, 9.4 mmol) at 5° C. and the mixture was stirred for 1 hr. at the same temperature. The mixture was diluted with EtOAc, washed with water, dried and concentrated in vacuo. The residue was chromatographed on a column of silica gel (80 g). The column was eluted with CHCl$_3$-MeOH (2%) and the fraction containing the desired product was evaporated in vacuo to give 1.62 g (69%) of the production.

MP 134°–137° C.

IR $\nu_{max}$(KBr) cm$^{-1}$ 2360, 2340, 1820, 1780, 1730. UV $\lambda_{max}$(EtOH) nm ($\epsilon$) 257 (17,700), 285 (12,500). $^1$H NMR (DMSO-d$_6$) $\delta$2.15 (3H, s, CH$_3$), 3.58 (2H, ABq, 2-H), 5.1 (2H, s, 4-CH$_2$), 5.2 (1H, d, J=5 Hz, 6-H), 5.1–5.8 (3H, m, CH=CH$_2$), 5.8 (1H, dd, 7-H), 6.6 (1H, s, thiazole), 7.3 (15H, s, phenyl), 9.51 (1H, d, J=8 Hz, CONH).

Procedure 23

(5-Methyl-2-oxo-1, 3-dioxolen-4-yl)methyl 7-[(Z)-2-(2-Aminothiazol-4-yl)-2-hydroxyiminoacetamido]-3-vinyl-3-cephem-4-carboxylate A mixture of the ester produced in Procedure 21 (1.50 g, 2 mmol) and 90% formic acid (3 ml) was stirred for 1 hr. at room temperature. The reaction mixture was diluted with EtOAc-ice water and adjusted to pH 3.5 with aq. NaOH. The organic layer was separated, washed with water, dried and evaporated under reduced pressure. The residue was crystallized from MEK to give 679 mg (67%) of the crystalline product.

MP 136°–139° C.

IR $\nu_{max}$(KBr) cm$^{-1}$ 2360, 2340, 1825, 1775, 1730. UV $\lambda_{max}$(EtOH) nm ($\epsilon$) 294 (15,600). $^1$H NMR (DMSO-d$_6$) $\delta$2.18 (3H, s, CH$_3$), 3.74 (2H, ABq, 2-H), 5.17 (2H, s, 4-CH$_2$), 5.20 (1H, d, J=5 Hz, 6-H), 5.1–5.7 (3H, m, CH=CH$_2$), 5.8 (1H, dd, J=5, 8 Hz, 7-H), 6.65 (1H, s, thiazole), 9.43 (1H, d, J=8 Hz, CONH).

Anal Calcd for C$_{19}$H$_{17}$N$_5$O$_8$S$_2$.2/5MEK .4/5 H$_2$O: C 44.93, H 3.99, N 12.72, S 11.64.

Found: C 45.03, H 3.55, N 12.79, S 11.37.

What is claimed is:

1. The process for the preparation of a physiologically hydrolyzable ester of Formula I

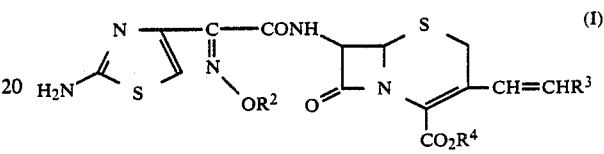

wherein R$^2$ is hydrogen, R$^3$ is hydrogen, or methyl, and R$^4$ is a physiologically hydrolyzable ester group consisting essentially of reacting under esterifying conditions an O-protected acid of Formula I wherein R$^4$ is hydrogen and R$^2$ is selected from the group consisting of trityl, (p-anisyl)diphenylmethyl, methoxymetyl, 2-methoxyethoxymethyl, 1-methoxy-1-methylethyl, and tertiary butyldimethylsilyl, and R$^3$ is as defined above with an esterifying agent capable of introducing the said R$^4$ physiologically hydrolyzable ester group; and thereafter replacing said R$^2$ O-protecting group with hydrogen by hydrolysis with formic, acetic, or trifluoroacetic acid.

2. The process for the preparation of 2-[(Z)-2-aminothiazol-4-yl]-2-(R$^2$O-imino)acetic acid wherein R$^2$ is selected from the group consisting of trityl, (p-anisyl)diphenylmethyl, methoxymethyl, 2-methoxyethoxymethyl, 1-methoxy-1-methylethyl, and tertiary butyldimethylsilyl which comprises reacting in the presence of one molecular proportion of sodium hydride, one molecular proporation each of a lower alkyl 2-[(Z)-2-aminothiazol-4-yl]-2-hydroxyiminoacetate having from 1 to 4 carbon atoms in the alkyl group, and a R$^2$ halide, said halide being chloro, bromo, or iodo in an anhydrous reaction inert liquid medium at room temperature, and hydrolyzing the lower alkyl 2-[(Z)-2-aminothiazol-4-yl]-2-(R$^2$O-imino)acetate so produced to the corresponding 2-[(Z)-2-aminothiazol-4-yl]-2-(R$^2$O-imino)acetic acid by treatment with about 3 molecular proportions of sodium hydroxide in 50% aqueous dioxane at the reflux temperature and recovering the desired acid.

3. The process for the preparation of 2-[(Z)-2-aminothiazol-4-yl]-2-(R$^2$O-imino)acetic acid lower alkyl ester wherein R$^2$ is selected from the group consisting of trityl, (p-anisyl)diphenylmethyl, methoxymethyl, 2-methoxyethoxymethyl, 1-methoxy-1-methylethyl, and tertiary butyldimethylsilyl and having 1 to 4 carbon atoms in the lower alkyl group which comprises reacting in the presence of one molecular proportion of sodium hydride, one molecular proportion each of a lower alkyl 2-[(Z)-2-aminothiazol-4-yl]-2-hydroxyiminoacetate having 1 to 4 carbon atoms in the alkyl group, and a R$^2$ halide, said halide being chloro, bromo, or iodo in an anhydrous reaction inert liquid medium at room temperature.

4. The process of claim 2 or 3 wherein $R^2$ is trityl.

5. The process of claim 2 or 3 wherein $R^2$ is (p-anisyl)diphenylmethyl.

6. The process of claim 1 wherein $R^2$ is trityl.

7. The process of claim 1 wherein $R^2$ is (p-anisyl)diphenylmethyl.

8. The process of claims 1, 6, or 7 wherein said esterifying conditions comprise reaction of said O-protected acid of Formula I wherein $R^4$ is hydrogen with a compound selected from the group consisting of 1-acetoxyethyl bromide, cyclohexyl 1-iodoethyl carbonate, 1-ethoxycarbonyloxyethyl iodide, and (5-methyl-2-oxo-1,3-dioxolen-4-yl)-methyl bromide in dimethylformamide solution in the presence of potassium carbonate and at a temperature of 0°–5° C.

9. The process of claims 1, 6, or 7 wherein said hydrolysis is carried out with 90% aqueous formic acid at room temperature.

* * * * *